US005874481A

United States Patent [19]
Weers et al.

[11] Patent Number: 5,874,481
[45] Date of Patent: *Feb. 23, 1999

[54] FLUOROCHEMICAL SOLUTIONS FOR THE DELIVERY OF LIPOPHILIC PHARMACEUTICAL AGENTS

[75] Inventors: Jeffry G. Weers, San Diego; Luis A. Dellamary, San Marcos; Thomas E. Tarara; Leo A. Trevino, both of San Diego; Helen M. Ranney, La Jolla, all of Calif.

[73] Assignee: Alliance Pharmaceutical Corp., San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 483,468

[22] Filed: Jun. 7, 1995

[51] Int. Cl.$^6$ .......................... A61K 31/02; A61K 31/045
[52] U.S. Cl. ........................ 514/761; 514/757; 514/724
[58] Field of Search ................................. 514/757, 761, 514/724

[56] References Cited

U.S. PATENT DOCUMENTS

| | | |
|---|---|---|
| 3,975,512 | 8/1976 | Long, Jr. . |
| 4,814,161 | 3/1989 | Jinks et al. . |
| 5,080,885 | 1/1992 | Long, Jr. ....................................... 424/5 |
| 5,114,703 | 5/1992 | Wolf et al. . |
| 5,208,226 | 5/1993 | Palmer ....................................... 514/171 |
| 5,230,884 | 7/1993 | Evans et al. . |
| 5,292,499 | 3/1994 | Evans et al. . |
| 5,653,961 | 8/1997 | McNally et al. ........................... 424/45 |
| 5,653,962 | 8/1997 | Akehurst et al. ........................... 424/45 |
| 5,658,549 | 8/1997 | Akehurst et al. ........................... 424/45 |
| 5,674,471 | 10/1997 | Akehurst et al. ........................... 424/45 |
| 5,674,472 | 10/1997 | Akehurst et al. ........................... 424/45 |
| 5,674,473 | 10/1997 | Purewal et al. ............................. 424/45 |
| 5,676,929 | 10/1997 | Akehurst et al. ........................... 424/45 |
| 5,683,677 | 11/1997 | Purewal et al. ............................. 424/45 |
| 5,688,782 | 11/1997 | Neale et al. ............................... 514/180 |
| 5,736,124 | 4/1998 | Akehurst et al. ........................... 424/45 |
| 5,744,123 | 4/1998 | Akehurst et al. ........................... 424/45 |

FOREIGN PATENT DOCUMENTS

| | | |
|---|---|---|
| 0255443 | 2/1988 | European Pat. Off. . |
| 0307087 | 3/1989 | European Pat. Off. . |
| 0311473 | 4/1989 | European Pat. Off. . |
| 0553298 | 11/1994 | European Pat. Off. . |
| 0616525 | 9/1995 | European Pat. Off. . |
| 9015807 | 12/1990 | WIPO . |
| 9104664 | 4/1991 | WIPO . |
| 9202560 | 2/1992 | WIPO . |
| 9218165 | 10/1992 | WIPO . |
| 9301798 | 2/1993 | WIPO . |
| 9311744 | 6/1993 | WIPO . |
| 9311745 | 6/1993 | WIPO . |
| 9414415 | 7/1994 | WIPO . |
| 9416742 | 8/1994 | WIPO . |
| 9517195 | 6/1995 | WIPO . |
| 9531182 | 11/1995 | WIPO . |
| 9533447 | 12/1995 | WIPO . |
| 9619197 | 6/1996 | WIPO . |
| 9619198 | 6/1996 | WIPO . |
| 9805302 | 2/1998 | WIPO . |
| 9808519 | 3/1998 | WIPO . |

OTHER PUBLICATIONS

Derwent Database Publications Ltd. AN 89–136216 Abstract for JP 01083015, Mar. 28, 1989.

Arbuck, et al. "Clinical Development of Taxol" J. of National Cancer Institute Monographs 15: 11–24 (1993).

Blair, et al. "Vitreoperfusion" Arch Opthalmol 107:417–423 (1989).

Hageluken, et al. "Lipophilic β–Adrenoceptor Antagonists and Local Anesthestics Are Effective Direct Activators of G–Proteins" Biochemical Pharmacology 47(10): 1789–1795 (1994).

Hughes, et al. "Effect of Acylation on the Ocular Disposition of Acyclovir II: Corneal Permeability and Anti–HSV 1 Activity of 2'–Esters in Rabbit Epithelial Keratitis" J. Ocular Pharmacology 9(4): 299–309 (1993).

Lewis, et al. "The Use of Perfluorocarbon Liquids in the Repositioning of Posteriorly Dislocated Intraocular Lenses"; Ophthalmology 100(7); 1055–1059 (1993).

Riess, Jean G. "Fluorocarbon–Based In Vivo Oxygen Transport and Delivery System" Vox Sanguinis 61: 225–239 (1991).

Shaffer, et al. "Perfluorochemical Liquid As A Respiratory Medium" Art. Cells, Blood Subs., and Immob. Biotech. 22(2): 315–326 (1994).

Shaffer, et al. "Liquid Ventilation" Pediatric Pulmonary 14: 102–109 (1992).

Tang–Liu, et al. "Lenticular Uptake and Distribution of Xenobiotics and Amino Acids" J. of Ocular Pharmacology 8(3): 267–277 (1992).

Wolfson, et al. "Pulmonary Administration of Drugs (PAD): A New Approach for Drug Delivery Using Liquid Ventilation" FASEB 4: A1105 (1990).

Yokogawa, et al. "Relationships in the Structure–Tissue Distribution of Basic Drugs in the Rabbit" Pharmaceutical Res. 7(7): 691–696 (1990).

Naito, et al. "Supplement to Perfluorochemical Blood Substitutes" Technical Information Series No. 5: 1–177 (1978).

(List continued on next page.)

*Primary Examiner*—William R. A. Jarvis
*Attorney, Agent, or Firm*—Knobbe, Martens, Olson & Bear, LLP

[57] ABSTRACT

A thermodynamically stable molecular solution providing enhanced bioavailability for lipophilic pharmaceutical agents, comprising a liquid carrier comprising one or more physiologically acceptable lipophilic fluorochemicals, and a pharmaceutically effective amount of at least one lipophilic pharmaceutical agent in said liquid carrier to form a thermodynamically stable molecular solution, optionally also including a co-solvent for facilitating solubilization of the pharmaceutical agent. Methods of making and using the molecular solution are also disclosed.

35 Claims, No Drawings

OTHER PUBLICATIONS

Naito, et al. "Supplement to Perfluorochemical Blood Substitutes" Technical Information Series No. 7: 1–119 (1981).

Rowinsky, et al. "Pacitaxel (TAXOL)" New England Journal of Medicine 332(15): 1004–1014 (1995).

Evans, et al. "Formulation and in Vitro Evaluation of Presurized Inhalation Aerosols Containing Isotropic Systems of Lecithin and Water" Pharmaceutical Res. 8(5): 629–635 (1991).

Banker, et al. *Modern Pharmaceutics*, ed. Marcel Dekker, Inc., New York pp. 31–49 (1991).

Balasubramanian, et al. "Taxol–Lipid Interactions: Taxol–Dependent Effects on the Physical Properties of Model Membrane" Biochemistry 33: 8941–8947 (1994).

Moriguchi, et al. "Simple Method of Calculating Octanol/Water Partition Coefficient" Chem. Pharm. Bull. 40(1): 127–130 (1992).

Prescott, L.F. "The Need for Improved Drug Delivery in Clinical Practice" Novel Drug Delivery and its Therapeutic Application Chapter 1 pp. 1–7, eds. Prescott, et al. (1988).

Riess, Jean. "Hemocompatible Fluorocarbon Emulsions" Blood Compatible Materials and Devices–Perspectives Towards the 21st Century Chapter 14 pp. 237–270, eds. Sharma, et al. (1991).

FLUOROCHEMICAL SOLUTIONS FOR THE DELIVERY OF LIPOPHILIC PHARMACEUTICAL AGENTS

FIELD OF THE INVENTION

The present invention generally relates to thermodynamically stable formulations and methods for the administration of lipophilic pharmaceutical agents to a physiological target site. More specifically, the invention is directed to improved molecular solutions that may be used to increase the bioavailability and efficacy of lipophilic agents having limited solubility in an aqueous physiologic environment. These solutions may be formulated so as to facilitate administration, increase bioavailability and enhance drug stability while avoiding complications associated with conventional fluorochemical suspensions and micellar solutions. Accordingly, they are particularly suitable for the sustained and controlled administration of lipophilic pharmaceutical agents to sensitive physiological sites such as the lung.

BACKGROUND OF THE INVENTION

The efficacy of many pharmaceutical agents is predicated on their ability to proceed to the selected target sites and remain there in effective concentrations for sufficient periods of time to accomplish the desired therapeutic or diagnostic purpose. Difficulty in achieving efficacy may be exacerbated by the location and environment of the target site as well as by the inherent physical characteristics of the compound administered. For example, drug delivery via routes that are subject to repeated drainage or flushing as part of the bodies natural physiological functions offer significant impediments to the effective administration of pharmaceutical agents. In this respect, delivery and retention problems are often encountered when administering compounds through the respiratory or gastrointestinal tracts. Repeated administration of fairly large doses are often required to compensate for the amount of drug washed away and to maintain an effective dosing regimen when employing such routes. Moreover, the molecular properties of the pharmaceutical compound may impair the absorption through a given delivery route, thereby resulting in a substantial reduction in efficacy. This is particularly true of lipophilic compounds that are not soluble in aqueous environments. For instance, insoluble particulates are known to be subject to phagocytosis and pinocytosis, resulting in the accelerated removal of the compound from the target site. Such reductions in delivery and retention time complicate dosing regimes, waste pharmaceutical resources and generally reduce the overall efficacy of the administered drug.

Unlike many hydrophilic compounds, the delivery of lipophilic drugs by conventional means has been and continues to be problematic. Unfortunately, a number of the most promising therapeutic and diagnostic agents currently under development are bulky polycyclic molecules that tend to be relatively insoluble in water. The substantial physical size of these compounds, coupled with the intrinsic lipophilicity of their molecular structure, has severely limited their use in practical pharmaceutical applications. For instance, the oral administration of lipophilic agents using conventional tablets and capsules suffers the disadvantage of a variable rate of absorption of the administered drug and depends on factors such as the presence or absence of food, the Ph of gastrointestinal fluids and gastric emptying rates. Moreover, the insolubility of large lipophilic particulates tends to reduce delivery rates as little drug dissolves in the gastrointestinal liquid and crosses the epithelial barrier before it is excreted. Finally, the degradation of labile drugs by gastric fluids and drug metabolizing enzymes may reduce the drug bioavailability to the point of therapeutic failure (Prescott, L. F., in Novel Drug Delivery and its Therapeutic Application, John Wiley & Sons, New York, 1989, pp. 3–4).

Other delivery routes fare little better when lipophilic compounds are administered using conventional delivery vehicles. The parenteral administration of these water insoluble drugs requires that they be formulated in the form of oil in water emulsions or that they be solubilized into a water miscible phase. This suffers drawbacks associated with the formulation of a suitably stable dosage form that can be delivered by this route; such formulations often contain surfactant systems which, by themselves, may cause toxic side effects. For example, the current method used for the intravenous administration of the highly lipophilic cancer drug Taxol involves the use of a polyoxyethylated castor oil vehicle that has been associated with hypersensitivity reactions including dyspnea, bronchospasm, urticaria, and hypotension (Rowinsky, E. K. and Donehower, R. C., New Eng. J. Med., 1995, 332, 1004). In addition, the intravenous administration of drugs such as Taxol, which exhibit high systemic toxicities, severely limits their therapeutic capacity (Balasubramanian, S. V. and Straubinger, R. M., Biochemistry, 1994, 33, 8941). Thus, despite encouraging results with existing delivery other reference systems, the inherently low bioavailability of these lipophilic compounds at the target site due to inefficient or toxic delivery systems substantially reduces their efficacy.

In spite of the difficulties associated with the delivery of lipophilic drugs, the potential advantages in developing methods to do so are great. Extensive work has been done to show that the membrane permeability, bioavailability and efficacy of drugs often increases with increasing lipophilicity (Banker G. S. and Rhodes, C. T. in "Modern Pharmaceutics", Marcel Dekker, Inc., New York, 1979, pp. 31–49; Hughes, P. M. and Mitra, A. K., J. Ocul. Pharmac., 1993, 9, 299; Yokogawa, K., Nakashima, E., Ishizaki, J., Maeda, H., Nagano, T. and Ichimura, F., Pharm. Res. 1990, 7, 691; Hageluken, A., Grunbaum, L., Nurnberg, B., Harhammer, R., Schunack, W. and Seifert, R., Biochem. Pharmac., 1994, 47, 1789). The development of new systems for the delivery of these compounds could, therefore, significantly increase the therapeutic efficacies for the treatment of a wide variety of indications.

In this respect, one class of delivery vehicles that has shown great promise when used for the administration of pharmaceutical agents is fluorochemicals. During recent years, fluorochemicals have found wide ranging application in the medical field as therapeutic and diagnostic agents. The use of fluorochemicals to treat medical conditions is based, to a large extent, on the unique physical and chemical properties of these substances. In particular, the relatively low reactivity of fluorochemicals allows them to be combined with a wide variety of compounds without altering the properties of the incorporated agent. This relative inactivity, when coupled with other beneficial characteristics such as an ability to carry substantial amounts of oxygen, radioopaqueness for certain forms of radiation and low surface energies, have made fluorochemicals invaluable for a number of therapeutic and diagnostic applications.

For example, various fluorochemical emulsions have been used as oxygen carriers during medical procedures. Conventional oil-in-water emulsions, which may be infused directly into the blood stream, consist of a selected fluorochemical dispersed in the form of droplets in a continuous aqueous phase. Because of the high oxygen-carrying capacity of fluorochemicals, such emulsions are particularly useful as blood substitutes to provide oxygen to the vascular system. After administration of the emulsions, the oxygen dissolved in the dispersed fluorochemical phase is released into the blood. "Fluosol" (Green Cross Corp., Osaka, Japan), a formerly commercially available oil-in-water emulsion containing fluorochemicals, has been used as a gas carrier to oxygenate the myocardium during percutaneous transluminal coronary angioplasty (R. Naito, K. Yokoyama, Technical Information Series No. 5 and 7, 1981). Fluorochemicals have also been used as contrast enhancement media in radiological imaging by Long (U.S. Pat. No. 3,975,512) and in nuclear magnetic resonance imaging (U.S. Pat. No. 5,114, 703). Other proposed medical uses include the treatment of cardiovascular and cerebrovascular diseases, coronary angioplasty, organ preservation and cancer therapy; diagnostic ultrasound imaging and veterinary therapy (Riess J. G., "Blood Compatible Materials and Devices": Perspective Towards the 21st Century, Technomics Publishing Co., Lancaster, Pa., Ch. 14, 1991; Riess, J. G., Vox. Sang., 61:225, 1991). Conventional direct fluorochemical emulsions have been described in, for example, EP-A-0 255 443, FR-A- 2 665 705, FR-A- 2 677 360, FR-A- 2 694 559, FR-A- 2 679 150, PCT/WO90/15807, EP-A-311473 and U.S. Pat. No. 3,975,512.

In addition to the aforementioned oil-in-water emulsion system, neat fluorochemicals and emulsions having a continuous fluorochemical phase have also been used in various medical applications. For instance, neat fluorochemicals are being evaluated for use in liquid ventilation applications. Currently one product, LiquiVent™ (Alliance Pharmaceutical Corp., San Diego, Calif.); is undergoing clinical trials for use in Respiratory Distress Syndrome (RDS). Such compositions could also be used in the treatment of premature infants with underdeveloped lungs. Another product, Imagent® GI, (Alliance Pharmaceutical Corp., San Diego, Calif.), an FDA approved diagnostic agent composed of a neat fluorochemical, is particularly useful for imaging the gastrointestinal (Imagent GI) tract. Fluorochemical liquids are also finding potential utility in eye surgery applications, such as the repositioning of posteriorly dislocated intraocular lenses and in the treatment of ocular ischemia (Lewis, H. and Sanchez, G., Ophthalmology, 1993, 100, 1055; Blair, N. P., Baker, D. S., Rhode J. P., and Solomon, M., Arch Ophthalmol, 1989, 107, 417).

While such applications are impressive, the ability to use fluorochemicals to reliably deliver effective amounts of pharmaceutical agents, either in conjunction with fluorochemical mediated therapy or in a separate dosing regime, would be of great benefit. The use of fluorochemical drug delivery vehicles would be particularly favorable for lipophilic drugs that are insoluble in aqueous solutions and present special problems in the aqueous physiological environment. For example, efficient pulmonary administration of pharmaceutical compounds, both lipophilic and hydrophilic, would be especially advantageous. Pulmonary administration of drugs constitutes a difficult problem because the introduction of compounds directly into the lungs cannot be effectively achieved by means of an aqueous solution or by fluorochemical emulsions wherein the continuous phase is also aqueous. Yet, as seen from the applications above, fluorochemicals may easily be introduced to the lung. Such direct administration is critical in the treatment of lung disease as poor vascular circulation of diseased portions of the lung reduces the effectiveness of intravenous drug delivery. In addition to treating pulmonary disorders, fluorochemical pharmaceutical formulations administered to the lung could also prove useful in the treatment and/or diagnosis of disorders such as RDS, impaired pulmonary circulation, cystic fibrosis and lung cancer. In addition to the pulmonary route of administration, fluorochemicals could advantageously be used for the administration of compounds via other routes such as topically, orally, intraperitoneally, or intraocularly.

Work in this area has shown that the pulmonary delivery of biological agents through the alveolar surface may be facilitated when accomplished in conjunction with liquid ventilation (Wolfson, M. R. and Shaffer, T. H., The FASEB J., 1990, 4, A1105), that is, using formulations having an oxygen rich fluorochemical continuous phase. The increased efficacy observed in compounds administered in conjunction with liquid ventilation to the impaired lung may be due to several factors, including the high spreading coefficients of some fluorochemicals on the pulmonary surface, an increase in alveolar surface area due to more effective lung inflation and the delivery of oxygen by the fluorochemical. Shaffer, et al., have also shown that pulmonary administration can increase the biological response of some drugs when compared to intravenous administration (Shaffer, T. H., Wolfson, M. R., Greenspan, J. S. and Rubenstein, S. D., Art. Cells, Blood Sub. & Immob. Biotech., 1994, 22, 315).

Yet, despite such successes, the administration of pharmaceutical compounds, particularly therapeutics designed for absorption by the body, is not without difficulties. A significant problem associated with conventional fluorochemical mediated drug delivery is that the large majority of drugs (lipophilic and hydrophilic) are insoluble in the fluorochemical phase. This may present a number of issues involving administration of the compound including stability, particle size, dose reliability, dispersion consistency and ultimately bioavailability. For example, the current method of pulmonary administration involves the preparation of a crude dispersion of the fluorochemical insoluble material and delivery by turbulent flow (Shaffer, T. H., Wolfson, M. R. and Clark, L. C., Pediatric Pulmonology, 1992, 14, 102). Yet, using this technique to deliver fluorochemical insoluble drugs (Shaffer et al., Art. Blood Subs. and Cells Immob. Biotech., 22:1994; Pediatr. Pulmonol., 14:102, 1992) resulted in non-homogenous, unreliable and irreproducible drug delivery due to the inefficient dispersion of the powdered agent in the fluorochemical phase. Moreover, while suitable delivery vehicles of comparable efficacy often exist for hydrophilic compounds, the choice for lipophilic agents is much smaller.

Drug suspensions in volatile chlorofluorocarbon propellants of the current art are often heterogeneous systems which usually require redispersion prior to use. Yet, obtaining a relatively homogeneous distribution of the pharmaceutical compound is not always easy in an "oily" fluorochemical. In addition, these formulations suffer from the disadvantage that they are prone to aggregation of the particles which, in the case of aerosol delivery, can result in clogging of the propellant system and inadequate delivery of the drug. Crystal growth of the suspensions via Ostwald ripening may also lead to particle size heterogeneity and can significantly reduce the shelf-life of the formulation. Another major problem with conventional dispersions, whether they are emulsions or suspensions, is particle coarsening. Coarsening may occur via several mechanisms such as flocculation, fusion, molecular diffusion, and coalescence. Over a relatively short period of time these processes can coarsen the formulation to the point where it is no longer usable. Comparable problems may occur in fluorochemical suspensions designed for other routes of administration such as through the gastrointestinal tract or ocular environment.

A further constraint on such conventional dispersions concerns the distribution of particle sizes. For oral administration, smaller drug particles or crystals, often on the order of 10 nm to 100 nm with large surface areas, are preferred due to their rapid diffusion for the delivery vehicle to the site of action. Unfortunately, it is generally not practical to produce particles having the optimal characteristics using conventional means such as airstreaming or grinding. Accordingly, many current formulations incorporate drug particulates having average particle diameters on the order of a few microns or more.

Several attempts have been made to solve these problems and provide efficient fluorochemical delivery vehicles. For instance, Evans et al. (Pharm. Res., 1991, 8, 629; U.S. Pat. 5,292,499; U.S. Pat. 5,230,884) and Jinks et al. (U.S. Pat. 4,814,161) disclose the use of highly volatile chlorofluorocarbon propellants stabilized by lipid surfactants to form micellar solutions for pulmonary drug delivery. Yet, neither teach the use of relatively nonvolatile fluorochemical liquid continuous media in these aerosol formulations. Rather they state that the inclusion of large proportions of high boiling components in these formulations is undesirable. Additionally, Evans et al. limit their disclosure to the solubilization of hydrophilic pharmaceutical compounds with no mention of incorporating hydrophobic compounds.

Accordingly, it is an object of the present invention to provide thermodynamically stable molecular solutions providing enhanced bioavailability for lipophilic pharmaceutical agents.

It is a further object of the present to provide surfactantless thermodynamically stable fluorochemical solutions for the administration of lipophilic pharmaceutical agents.

It is yet a further objective of the present invention to provide stable fluorochemical pharmaceutical solutions for use in partial liquid breathing therapy.

Still another objective to provide thermodynamically stable fluorochemical solutions incorporating lipophilic pharmaceutical agents having extended shelf-lives.

SUMMARY OF THE INVENTION

In a broad aspect, the present invention accomplishes these and other desired objectives by providing novel, thermodynamically stable fluorochemical molecular solutions. More particularly, the present invention provides molecular solutions comprising one or more physiologically acceptable lipophilic fluorochemicals and a pharmaceutically effective amount of at least one lipophilic pharmaceutical agent. In direct contrast to prior art pharmaceutical compositions employing a fluorochemical delivery vehicle, the formulations of the present invention are true molecular solutions, rather than micellar solutions. That is, the incorporated lipophilic pharmaceutical agent or agents is dissolved by or in solution with the liquid carrier rather than associated with reverse micelles in an unstable discontinuous phase. Accordingly, the pharmaceutical solutions of the present invention may be formed without the use of surfactants.

The unexpected discovery that effective concentrations of lipophilic pharmaceutical agents could be placed in solution with physiologically acceptable lipophilic fluorochemicals allows for highly efficacious pharmaceutical solutions. Specifically, the stable solutions formed according to the teachings herein may be used to significantly increase the bioavailability and efficacy of lipophilic agents having limited solubility in an aqueous environment. These solutions may be formulated so as to facilitate administration, enhance drug stability and attenuate delivery profiles while avoiding complications associated with conventional fluorochemical suspensions and micellar solutions. Accordingly, they are particularly suitable for the sustained and controlled administration of lipophilic pharmaceutical agents to sensitive physiological sites such as the lung and gastrointestinal tract. At the same time they avoid complications associated with thermodynamically unstable dispersions such as coarsening.

More particularly, in one aspect, the present invention comprises a thermodynamically stable molecular solution providing enhanced bioavailability for lipophilic pharmaceutical agents. This solution comprises a pharmaceutically effective amount of at least one lipophilic pharmaceutical agent in a liquid carrier comprising one or more physiologically acceptable lipophilic fluorochemicals. In preferred embodiments the liquid carrier may further comprise a nonfluorinated (or non-fluorocarbon) co-solvent. Such co-solvents may advantageously be from the group consisting of ethers, alcohols, dimethyl foramide, alkyl sulfoxides, and combinations thereof. Preferably, the co-solvent is entirely miscible with the selected lipophilic fluorochemicals and forms a homogeneous solution.

Another aspect of the present invention relates to methods for preparing thermodynamically stable molecular solutions exhibiting enhanced bioavailability. The method comprises providing a liquid carrier comprising one or more physiologically acceptable lipophilic fluorochemicals and combining a pharmaceutically effective amount of at least one lipophilic pharmaceutical agent. Once again, in preferred embodiments the liquid carrier may further comprise a nonfluorinated co-solvent miscible with the lipophilic fluorochemical or fluorochemicals. Preferably the optional co-solvent is selected from the group consisting of ethers, alcohols, alkyl sulfoxides and combinations thereof. In such embodiments the co-solvent may comprise up to about 50% v/v and more preferably up to about 10% v/v.

Yet another aspect of the present invention relates to a method for delivering one or more lipophilic pharmaceutical agents to a physiologic target site. This method comprises the steps of providing a pharmaceutical solution with at least one lipophilic pharmaceutical agent incorporated in a physiologically acceptable liquid carrier wherein the liquid carrier comprises one or more lipophilic fluorochemicals. This pharmaceutical solution, containing an effective amount of the pharmaceutical agent or agents in solution, is then introduced to a physiologic target site. In preferred embodiments the thermodynamically stable pharmaceutical solution further comprises at least one co-solvent.

It should be emphasized that, in preferred embodiments, the formulations may be administered using a number of different routes including, but not limited to, the gastrointestinal tract, the respiratory tract, topical, intramuscular, intraperitoneal, nasal, pulmonary, vaginal, rectal, aural, oral or intraocular routes. Similarly, any lipophilic pharmaceutical agent that may be placed into solution to form the desired molecular solution may be effectively administered using the method outlined above. Preferably, the pharmaceutical agents will have a log of the octanol/water partition coefficient of at least 0.5, and more preferably of at least 2 while comprising less than about 10% w/v of the administered solution. Preferably, the solutions of the present invention may also incorporate a therapeutically beneficial amount of a physiologically acceptable gas, such as oxygen.

Other objects, features and advantages of the present invention will be apparent to those skilled in the art from a consideration of the following detailed description of preferred exemplary embodiments thereof.

DETAILED DESCRIPTION OF THE EXEMPLARY EMBODIMENTS

In a broad aspect, the thermodynamically stable molecular solutions of the present invention allow for the effective delivery of lipophilic or ethanol soluble nonionic pharmaceutical agents. As such compounds are relatively insoluble in water, their potential efficacy has generally been reduced when used with conventional drug delivery vehicles. The broadest form of the invention relates to a thermodynamically stable molecular solution having a solvent comprising one or more lipophilic fluorochemicals and a solute comprising one or more lipophilic pharmaceutical agents. Unlike prior art fluorochemical suspensions or emulsions, the solubilization of lipophilic pharmaceutical agents in the liquid carriers of the present invention allows for their effective delivery to aqueous physiological target sites. Those skilled in the art will further appreciate that, due to the bacteriostatic, nonirritating, and in fact, soothing and lubricating properties of the fluorochemical solutions, the formulations of the present invention are extremely well-suited for use in applications where repeated or prolonged administration is required. Other aspects of the present invention are related to methods for forming the disclosed solutions and methods for their administration to a physiologic target site.

In order to fully appreciate the unique and unexpected characteristics of the present invention, it must be emphasized that the formulations of the present invention are thermodynamic molecular solutions rather than micellar solutions, emulsions or fluorochemical suspensions. Thermodynamically stable solutions are those that form spontaneously under the appropriate conditions and will remain stable unless subjected to externally induced stress. In the present invention, effective concentrations of the selected pharmaceutical agent may be placed into solution at room temperature without extensive mixing. This is in sharp contrast to the complex formulation techniques required to produce a number of the prior art fluorochemical pharmaceutical compositions. Further, the formation of a molecular solution increases the bioavailability of the pharmaceutical agent at the selected target site. This, in turn, allows a reduction in dosage while achieving the same therapeutic effect, thereby lowering costs and improving the efficacy of the treatment by simplifying the dosing regimen.

Besides the lipophilic fluorochemical solvent, the pharmaceutical solutions of the present invention may further comprise a co-solvent to increase the solubility of the selected lipophilic pharmaceutical agent. In preferred embodiments, the co-solvent may be selected from the group consisting of alcohols, ethers, alkyl sulfoxides and combinations thereof. In particularly preferred embodiments the co-solvent will be ethanol. The co-solvent, while not necessary to practice the current invention, may substantially increase the solubility of selected lipophilic pharmaceutical agents.

It should be emphasized that the formation of the thermodynamically stable solutions is related to the relative lipophilicity of the solvent and solute components. That is, the lipophilicity of one component will influence the selection of the other components that are compatible with the invention. More particularly, the one or more lipophilic liquid fluorochemicals used in the liquid carrier must be sufficiently hydrophobic, alone or combined with at least one co-solvent, to incorporate the lipophilic pharmaceutical agent or agents of interest into a thermodynamically stable molecular solution. Accordingly, the choice of lipophilic fluorochemical will be influenced by the lipophilicity of the pharmaceutical agents that are to be incorporated.

Although the scope of the invention is defined by the formation of the desired solutions, some indication of which components will operate in combination to produce the preferred results may be obtained from a comparison of their lipophilicity as determined by methods well known in the art. The lipophilicity of a compound can be related to several different parameters including the critical solution temperature in n-hexane (CSTH), the molar refraction ($R_m$) and the logarithm of the octanol-water partition coefficient (log $P_{o/w}$). While each of these methods are commonly used to determine the lipophilicity of different agents, certain methods are preferred for different classes of compounds. For instance, the lipophilicity of pharmaceutical compounds are typically measured and reported using the octanol-water partition coefficient (log $P_{o/w}$). Conversely, the lipophilicity of liquid fluorochemicals is generally determined using the critical solution temperature in n-hexane and the molar refraction ($R_m$) methods, with the CSTH standard being the more common of the two. For the purposes of describing the present invention this convention will be followed. Accordingly, for purposes of explanation only, exemplary lipophilicity values for pharmaceutical agents will be provided as determined by the octanol-water partition coefficient while exemplary lipophilicity values for liquid fluorochemicals will be provided as determined by using the molar refractivity procedure.

Those skilled in the art will appreciate that the critical solution temperature in n-hexane is defined to be the temperature at which an equivolume mixture of n-hexane and the substance to be measured form two immiscible phases. The values derived using this empirical technique generally correspond to the relative lipophilicity of compounds as determined using molar refraction. The molar refraction is calculated by the following equation:

$$R_m = V_m(n^2-1)/(n^2+2) \qquad \text{Eq. 1}$$

where, $V_m$ and n are the molar volume and refractive index, respectively. Generally, for a class of compound, having the same number of carbons, the lower the value obtained, the more lipophilic the compound. For the purposes of this application the $R_m$ values were calculated using a computer model based on group contribution-additivity and quantum mechanical behavior based on empirical observations. Accordingly, the values contained herein are estimates of lipophilicity offered for purposes of explanation only and in no way limit the scope of the invention.

Finally, the octanol-water partition coefficient is the ratio of the amounts of a substance that partition between equal volumes of octanol and water. That is, the lipophilic substance to be measured is in solution in an immiscible octanol/water mixture and the amount of substance in each phase is subsequently measured. As reported in the literature, the higher the value obtained, the more lipophilic the substance in question.

Due to the low polarizability of highly fluorinated compounds, the solubilities of nonfluorinated substances, including many lipophilic drugs, in fluorochemicals is very low. In order to incorporate pharmaceutically effective amounts of lipophilic agents in fluorochemicals, the fluorochemicals used must be relatively lipophilic in nature. The lipophilicity of fluorochemicals can be significantly increased by substituting for fluorine atoms with more polarizable groups. Substituents which are particularly effective are polarizable halogens (i.e. Br, Cl, I) and hydrocarbon chains.

More particularly, lipophilic fluorochemicals, or combinations of lipophilic fluorochemicals which are capable of promoting the dissolution and incorporation of the selected lipophilic agent or agents into the thermodynamically stable solutions of the present invention are preferred. Exemplary lipophilic fluorochemicals which are particularly suited for use in the invention contain one or more nonfluorine halogen atoms (i.e. bromine, chlorine, iodine), a hydrocarbon substituent group (i.e. —$C_2H_5$) or an amine group. In a preferred embodiment, the fluorochemical contains up to ten carbons. In a particularly preferred embodiment, the fluorochemical contains between four and eight carbons. The molecular structures of the fluorochemicals used to form the thermodynamically stable molecular solution may be linear, branched or contain cyclic structures. They may also be saturated, unsaturated or contain aromatic groups.

The ability to use different fluorochemicals to form stable molecular solutions in accordance with the teachings herein is particularly advantageous as the particular fluorochemical may be selected based, at least in part, on secondary characteristics of the fluorocarbon. For example, if two or more lipophilic perfluorochemicals are equally effective in forming the desired solution, the perfluorochemical ultimately selected may be chosen to provide a solution having certain specific physical characteristics such as volatility or viscosity or may be selected based on nontechnical criteria such as cost and availability.

As discussed above, any lipophilic fluorochemical capable of incorporating the selected lipophilic pharmaceutical agent into a thermodynamically stable molecular solution is compatible with the teachings herein and within the scope of the invention. That is, the lipophilic fluorochemicals which can be used in the current invention are defined by the selected lipophilic pharmaceutical agent. Yet, as an indication of which lipophilic fluorochemicals may be particularly beneficial, molar refractivity values and critical solution temperatures in n-hexane (CSTH) may be considered. Preferably the relatively lipophilic fluorochemicals used to incorporate the selected pharmaceutical agent will have molar refractivity values less than about 45 $cm^3$ or CSTH values of less than about 10° C. In particularly preferred embodiments, the relatively lipophilic perfluorochemicals will have molar refractivity values less than about 40 $cm^3$ or CSTH values of less than about −20° C. In one exemplary embodiment of the invention, the lipophilic fluorochemical is 1,4-dibromo-F-butane which has a molar reactivity value of approximately 36.68 $cm^3$. Table 1, immediately below, lists the molar refractivity values of this lipophilic fluorochemical and others which are compatible with the present invention.

TABLE 1

Molar refractivity values for relatively lipophilic fluorochemicals

| Fluorochemical | Estimated Molar Refractivity ($R_m$) (cm3) |
|---|---|
| n-Br$C_4F_8$Br | 36.68 |
| n-$C_4F_9$ $C_4H_9$ | 40.59 |

TABLE 1-continued

Molar refractivity values for relatively lipophilic fluorochemicals

| Fluorochemical | Estimated Molar Refractivity ($R_m$) (cm3) |
|---|---|
| n-$C_4F_9$ $C_2H_5$ | 31.38 |
| n-Cl$C_4F_8$Cl | 32.26 |

More particularly, exemplary lipophilic fluorochemicals which are contemplated for use in forming the thermodynamically stable molecular solutions of the present invention include the halogenated fluorochemicals (i.e. $C_nF_{2n+1}X$, $XC_nF_{2n}X$, where n=3–8, X=Br, Cl or I), fluorocarbon-hydrocarbon diblock or triblock compounds (i.e. $C_nF_{2n+1}$—$C_mH_{2m+1}$, $C_nF_{2n+1}CH=CHC_mH_{2m+1}$, where n=2–8; m=2–6 or $C_pH_{2p+1}$—$C_nF_{2n}$—$C_mH_{2m+1}$, where p=2–6, m=2–6 and n=2–8), halogenated ethers or polyethers (i.e. $XC_nF_{2n}OC_mF_{2m}X$, $XCF_2OC_nF_{2n}OCF_2X$, where n, m=1–4, X=Br, Cl or I) and fluorocarbon-hydrocarbon ether diblocks or triblocks (i.e. $C_nF_{2n+1}$—O—$C_mH_{2m+1}$, where n=2–8; m=2–6 or $C_pH_{2p+1}$—O—$C_nF_{2n}$—O—$C_mH_{2m+1}$, where p=2–6, m=2–6 and n=2–8).

Fluorocarbon-hydrocarbon compounds containing other linkage groups, such as esters, thioesters, amines and amides are also suitable for use in forming the thermodynamically stable molecular solutions of the present invention. Mixtures of fluorochemicals are also contemplated. Other suitable fluorochemicals may include the brominated perfluorocarbons, such as 1-bromo-F-octane (n-$C_8F_{17}$Br), 1-bromo-F-heptane (n-$C_7F_{15}$Br), and 1-bromo-F-hexane (n-$C_6F_{13}$Br) 1-bromo-F-pentane (n-$C_5F_{11}$Br); 1-bromo-F-butane (n-$C_4F_9$BR). Also contemplated are fluorochemicals having nonfluorine substituents, such as perfluorooctyl chloride (n-$C_7F_{15}$Cl), 1, 6-dichloro-F-hexane (n-Cl$C_6F_{12}$Cl), and 1, 4-dichloro-F-butane (n-Cl$C_4F_8$Cl). 1, 4-dibromo-F-butane and 1,6-dibromo-F-hexane are particularly preferred.

In addition to their relatively high lipophilicty, the preferred lipophilic fluorochemicals have vapor pressures sufficiently low to prevent significant liquid loss caused by evaporation during storage or delivery. As previously mentioned, some fluorochemicals have relatively high vapor pressures and correspondingly low boiling points which render them less suitable for use in the present invention. In particular, such volatile compounds are less useful for partial liquid breathing and pulmonary administration of drugs. Lower vapor pressures are additionally important from an economic standpoint since significant percentages of fluorochemical having high vapor pressure would be lost due to vaporization during storage or the therapies described herein. More specifically, lipophilic fluorochemicals having ambient pressure boiling points greater than about 37°.

As pulmonary delivery of drugs is an important aspect of the present invention, the fluorochemicals chosen may advantageously have functional characteristics that would permit their use temporarily as a lung surfactant, for oxygen delivery, in removal of material from the interior of the lung, or for inflation of collapsed portions of the lung. Fluorochemicals are biocompatible and most are amenable to sterilization techniques. For example, they can be heat-sterilized (such as by autoclaving) or sterilized by radiation. In addition, sterilization by ultrafiltration is also contemplated.

In normal physiological systems, surfactants function to decrease the tension between the surface molecules of the alveolar fluid. The lung surfactant is present in a water-continuous fluid lining the alveolus. Typically, the surface tension in the absence of lung surfactant is ca. 70 dynes/cm decreasing to almost 0 dynes/cm in the presence of lung surfactant. Fluorochemicals have low surface tension values (typically in the range of 20 dynes/cm) and have the added benefit of dissolving extremely large quantities of gases such as oxygen and carbon dioxide. Perfluorochemicals are particularly suited for this use, and brominated fluorochemicals are particularly preferred. Moreover, the low surface tension imparted by the fluorochemical continuous phase of the present invention increases the bioavailability of the incorporated pharmaceutical agent, and thereby increases its efficacy.

Although reduction in surface tension is an important parameter in judging fluorochemicals and perfluorochemicals as pulmonary delivery vehicles, or for use in partial liquid breathing, a novel and non-obvious characteristic of some fluorochemicals is their apparent ability to spread over the entire respiratory membrane. Like the ability of fluorochemicals to reduce surface tension, the ability of some fluorochemicals to spread evenly and effectively over lung surfaces may increase the bioavailability, and hence the uptake of the incorporated pharmaceutical agent. Accordingly, the solutions of the present invention are particularly suited for the pulmonary administration of pharmaceutical agents through such techniques as partial liquid ventilation or aerosol delivery.

The total surface area of the respiratory membrane is extremely large (ca. 160 square meters for an adult). As such, an effective fluorochemical for partial liquid breathing and concurrent drug delivery should be able to cover the lung surfaces with relatively little volume.

The ability of a given substance to cover a measured surface area can be described by its spreading coefficient. The spreading coefficients for fluorochemicals can be expressed by the following equation:

$$S (o \text{ on } w) = \gamma w/a - (\gamma w/o + \gamma o/a) \qquad \text{Eq. 2}$$

Where S (o on w) represents the spreading coefficient (oil on water); γ=interfacial tension; w/a=water/air; w/o=water/oil; and o/a=oil/air.

If the fluorochemical exhibits a positive spreading coefficient, then it will spread over the entire surface of the respiratory membrane spontaneously. Fluorochemicals having positive spreading coefficients are particularly preferred for use in pulmonary drug administration. Of course, it must be emphasized that fluorochemicals with lower coefficients may also be used to formulate solutions in accordance with the present invention and used for the effective administration of drugs, including pulmonary administration. In addition to enhancing the bioavailability of the incorporated pharmaceutical agent, adequate coverage of the lung surface is beneficial for restoring oxygen and carbon dioxide transfer and for lubricating the lung surfaces to minimize further pulmonary trauma. In this respect, fluorochemicals compatible with the present invention are generally able to promote gas exchange. Accordingly, in preferred embodiments, the molecular solutions of the present invention will be enriched through the introduction and incorporation of a physiologically acceptable gas, such as oxygen.

In addition to lipophilic fluorochemicals, the molecular solutions of the present invention may optionally contain at least one nonfluorinated co-solvent to facilitate the dissolution of the lipophilic pharmaceutical agent in the thermodynamically stable solution. Preferably this co-solvent is entirely miscible with the selected lipophilic fluorochemical and comprises up to about 50%, v/v, of the thermodynamically stable solution. In a most preferred embodiment, the concentration of the nonfluorinated co-solvent comprises up to about 20%, v/v, of the thermodynamically stable solution.

Exemplary embodiments of the invention preferably include a co-solvent selected from the group consisting of ethers, alcohols, alkyl sulfoxides and combinations thereof. Co-solvents which are particularly suitable for use with the present invention are short chain alcohols (i.e., carbon chain length ≦4 carbons) or an alkyl sulfoxides such as dimethylsulfoxide. In a particularly preferred embodiment the co-solvent is ethanol.

As alluded to previously, the molecular solutions disclosed herein may further comprise one or more additives. The additives, which may be in particulate form or in solution, include for example mineral salts, buffers, oncotic and osmotic agents, nutritive agents, flavorings or palatability enhancers, or any other ingredient capable of augmenting the favorable characteristics of the molecular solutions including pharmaceutical stability, therapeutic efficacy and tolerance.

The solutions of the present invention are capable of delivering any desired pharmaceutical agent that may be dissolved or otherwise in solution in the selected liquid carrier. As used herein, the term pharmaceutical agent is defined to mean any therapeutic, bioactive, or diagnostic compound or composition which may be administered to an animal. Preferred pharmaceutical agents include nonionic drugs with solubility in ethanol and lipophilic drugs. Most preferably, the incorporated pharmaceutical agents are lipophilic agents.

Preferably, the lipophilic pharmaceutical solutions of the present invention incorporate less than about 10% w/v of a therapeutic or diagnostic agent. The precise amount of pharmaceutical agent incorporated in the solutions of the present invention is dependent upon the agent of choice, the required dose, and the form of the drug actually incorporated in the solution. Those skilled in the art will appreciate that such determinations may be made by using well known techniques in combination with the teachings of the present invention.

Preferred pharmaceutical agents comprise respiratory agents, antibiotics, antivirals, mydriatics, antiglaucomas, anti-inflammatories, antihistaminics, antineoplastics, anesthetics, ophthalmic agents, cardiovascular agents, active principles, nucleic acids, genetic material, immunoactive agents, imaging agents, immunosuppressive agents, gastrointestinal agents and combinations thereof. Further exemplary embodiments of the present invention comprise anti-inflammatory agents such as the glucocorticosteroids (i.e. cortisone, prednisone, prednisolone, dexamethasone, betamethasone, Beclomethasone diproprionate, Triamcinolone acetonide, Flunisolide), xanthines (i.e. theophylline, caffeine), chemotherapeutics (i.e. cyclophosphamide, lomustine, methotrexate, cisplatin, taxane derivatives), antibiotics (i.e. aminoglycosides, penicillins, cephalosporins, macolides, quinolones, tetracyclines, chloramphenicol), bronchodilators such as the $B_2$-agonists (i.e. adrenaline, isoprenaline, salmeterol, albuterol, salbutamol, terbutaline, formoterol) and surfactants. Still other exemplary embodiments include α/B adrenergic blockers (i.e. Normodyne®, Trandate®), angiotensin converting enzyme inhibitors (i.e. Vasotec®), antiarrhythmics, beta blockers, calcium channel blockers, inotropic agents, vasodilators, vasopressors, anesthetics (i.e. morphine) and ophthalmic agents (i.e. Polymyxin B, Neomycin, Gramicidin).

Most preferred agents include, glucocorticosteroids, taxane derivatives (i.e. Taxol Taxotere™) and the base forms of drugs typically administered as the salt derivative (i.e. Gentimicin, Ciprofloxacin). In accordance with the present invention, those skilled in the art will appreciate that various forms of these compounds may be used to modify the therapeutic index of the pharmaceutically active agents.

Similar to the fluorochemicals discussed above, the selection of compatible lipophilic pharmaceutical agents is limited only by the ability to place them in solution in the liquid carrier as disclosed herein and form the desired molecular solution. Yet, some indication as to the compatibility of an individual pharmaceutical agent may be derived from the measured value of its lipophilicity. Unlike the fluorochemical components of the present invention, the convention is to measure and report the lipophilicity of a pharmaceutical compound using the log of the octanol/water partition coefficient (Log $P_{o/w}$. In this system, increasing lipophilicity corresponds to higher Log $P_{o/w}$ values. Preferably, the lipophilic agents incorporated in the present invention will have a Log $P_{o/w}$ greater than about 0.5. More preferably, the pharmaceutical agents will have a Log $P_{o/w}$ greater than about 2.0. As those skilled in the art will appreciate, values such as these indicate that a compound has limited solubility in an aqueous environment. Accordingly, and for the purpose of explanation only, the octanol/water partition coefficients of several exemplary lipophilic pharmaceutical agents compatible with the teachings of the present invention are reproduced below in Table 3.

TABLE 3

Octanol/water partition coefficients (Po/w) of various drugs

| Drug Substance | $P_{o/w}$ | Log $P_{o/w}$ |
|---|---|---|
| $^{14}$C-anthracene[1] | 3.16 × 10$^4$ | 4.5 |
| $^{14}$C-bunolol[1] | 2.51 × 10$^2$ | 2.4 |
| $^{14}$C-cimetidine[1] | 2.51 | 0.4 |
| $^{14}$C-hexamethylene lauramide[1] | 2.00 × 10$^7$ | 7.3 |
| $^{14}$C-padimate-o[1] | 3.98 × 10$^6$ | 6.6 |
| $^{14}$C-progesterone[1] | 7.9 × 10$^3$ | 3.9 |
| $^{14}$C-testosterone[1] | 2.00 × 10$^3$ | 3.3 |
| $^3$H-clonidine[1] | 25.1 | 1.4 |
| $^3$H-diethylstilbesterol[1] | 1.26 × 10$^5$ | 5.1 |
| $^3$H-fluorometholone[1] | 1.26 × 10$^2$ | 2.1 |
| $^3$H-parsol 1789[1] | 5.0 × 10$^6$ | 6.7 |
| valeryl acyclovir[2] | 2.01 | 0.30[a] |
| hexanoyl acyclovir[2] | 8.58 | 0.93[a] |
| lidocaine[3] | 2.88 | 0.46 |
| bupivacaine[3] | 28.2 | 1.45 |
| tetracaine[3] | 79.4 | 1.90 |
| halothane[4] | 2.00 × 10$^2$ | 2.30 |
| ampicillin[4] | 11.5 | 1.06 |
| oxazepam[4] | 1.78 × 10$^2$ | 2.25 |
| pentazocin[5] | 150 | 2.18[a] |
| nitrazepam[5] | 162 | 2.21[a] |
| haloperidol[5] | 485 | 2.69[a] |
| biperiden[5] | 678 | 2.83[a] |
| diazepam[5] | 970 | 2.99[a] |
| promethazine[5] | 1.27 × 10$^3$ | 3.10[a] |
| trihexyphenidyl[5] | 1.47 × 10$^3$ | 3.17[a] |
| chlorpromazine[5] | 1.90 × 10$^3$ | 3.28[a] |
| clotiazepam[5] | 3.06 × 10$^3$ | 3.49[a] |
| clomipramine[5] | 3.80 × 10$^3$ | 3.58[a] |

[1]Tang-Liu, D. D. -S., Richman, J. B. and Liu, S. S., J. Ocul. Pharmac., 1992, 8, 267
[2]Hughes, P. M. and Mitra, A. K., J. Ocul. Pharmac., 1993, 9, 299.
[3]Hageluken, A., Grunbaum, L., Nurnberg, B., Harhammer, R., Schunack, W. and Seifert, R., Biochem. Pharmac., 1994, 47, 1789.
[4]Moriguchi, I., Hirono, S., Liu, Q., Nakagome, I. and Matsuchita, Y., Chem. Pharm. Bull., 1992, 40, 127.
[5]Yokogawa, K., Nakashima, E., Ishizaki, J., Maeda, H., Nagano, T. and Ichimura, F., Pharm. Res. 1990, 7, 691.
[a] in octanol/pH 7.4 isotonic phosphate buffer at 37° C.

Because the solutions of the present invention are uniquely suited for use in a wide variety of physiological applications such as ocular, oral, pulmonary, rectal, subcutaneous, intramuscular, intraperitoneal, nasal, vaginal, or aural administration of medicaments or diagnostic compounds, a wide variety of pharmaceutical agents may be incorporated therein. Accordingly, the foregoing list of pharmaceutical agents is not intended to limit the present invention in any way.

Another unique advantage provided by the solutions of the present invention is the ability to use the free base form of the incorporated pharmaceutical agent rather than its less efficacious salt form. That is, the efficacy of lipophilic forms of drugs have been shown in many instances to be more potent than the less lipophilic forms of the drug, i.e. the salts. The nonreactive nature of the fluorochemical solutions allow the incorporation of particularly efficacious base forms of the selected pharmaceutical agent. As those skilled in the art will appreciate, the use of these more potent drug forms enhances the bioavailability of the incorporated pharmaceutical agent and reduces the dosages which must be administered.

It will also be appreciated by those skilled in the art that the proper amount of pharmaceutical and the timing of the dosages may be determined for the formulations in accordance with already-existing information and without undue experimentation.

More particularly, the fluorochemical solutions can be administered via several different routes, depending upon the indication to be treated. For example, intranasal or intrapulmonary administration (i.e. endotracheal tube or pulmonary catheter), aerosolization or nebulization is contemplated for the treatment of respiratory or systemic disorders. An example would include the treatment of lung cancer or other systemic cancers with taxane derivatives by the pulmonary administration of these drugs. Due to its low aqueous solubility, paclitaxel (i.e. Taxol) is conventionally formulated in a mixture of polyoxyethylated castor oil and ethanol (Bristol Meyers Squibb) which is intended for intravenous administration. In addition to manifestations of hypersensitivity associated with the delivery vehicle itself (i.e., bronchospasm and hypotension), other systemic toxicities associated with paclitaxel, such as cardiac toxicity and neurotoxicity, limit the potential usefulness of this drug (Arabic, S. G., Christian, M. C., Fisherman, J. S., Cazenave, L. A., Sarosy, G., Suffness, M., Adams, J., Canetta, R., Cole, K. E., and Friedman, M. A., J. Natl. Canc. Inst. Monogr, 1993, No. 15, 11.) The administration of paclitaxel via the intrapulmonary route in the form of a fluorochemical solution could significantly improve the safety profile of the drug by eliminating the use of biologically active delivery vehicles and by reducing the concentration of the drug in the circulation required for drug efficacy. Intraperitoneal, subcutaneous and ocular administration are also contemplated.

The fluorochemical solutions of the invention may also be used to deliver therapeutic and diagnostic agents to the gastrointestinal tract by the oral route of administration. A contemplated example would be the delivery of antibiotics to the lining of the gastrointestinal tract in the treatment of Heliobacter pylori infections. H. pylori has been implicated in the cause of gastric ulcers and stomach cancer. Antibiotics effective in the treatment of H. pylori infections could be administered in the form of lipophilic fluorochemical molecular solutions.

As discussed, the solutions of the present invention may be prepared by dissolving a lipophilic pharmaceutical agent using a liquid carrier comprising at least one lipophilic fluorochemical. In preferred embodiments, at least one non-fluorinated co-solvent may also be included in the liquid carrier.

It is contemplated that the solutions of present invention may be sterilized, for example, by autoclaving at 121° C. for 15 minutes, by irradiation, or by filtration through a 0.22 μm filter. Unlike prior art aqueous based pharmaceutical formulations that will support bacterial growth if preservatives are not used, the sterile solutions of the present invention have bacteriostatic properties. These bacteriostatic characteristics make it possible to provide pharmaceutical solutions without added preservatives and the associated possibility of attendant side effects. This is particularly advantageous for patients who exhibit sensitivity to preservatives.

Preferably, the sterile solutions are packaged and supplied to physicians in single or multidose forms. Due to the natural antimicrobial properties of the present invention, once the solutions are sterilized and packaged in multidose configurations they may be repeatedly opened without the growth of harmful organisms.

It is believed that the pharmaceutical solutions produced in accordance with the teachings of the present invention have unexpectedly improved shelf-lives when compared with comparable pharmaceutical compositions stored as dispersions or stored in a sterile dry state. In addition to the nonreactive, preservative characteristics of the fluorochemical, the molecular solutions of the invention are not subject to settling or degradation through coarsening, as are dispersions in the form of emulsions or suspensions. Accordingly, they remain viable and pharmaceutically active over an extended period of time. This is particularly true of the more potent ether, base or free alcohol forms of the pharmaceutical agent.

The following nonlimiting examples of various exemplary formulations of the present invention illustrate exemplary methods for the their formation and resultant characteristics.

In order to demonstrate the advantages of the present invention and demonstrate its widespread applicability, several lipophilic pharmaceutical agents were used to form thermodynamically stable pharmaceutical molecular solutions as described above. In this respect the following examples are intended to exemplify the operation of the present invention but not to limit its scope.

EXAMPLE 1

Preparation of a Diazepam in a Perfluorooctyl Ethane (n-C8F17 C2H5)/n-C6F13 C14H29 Solution A diazepam-containing perfluorochemical solution was prepared as follows:

An aliquot of $n$-$C_6F_{13}C_{14}H_{29}$ (1 g; F-Tech, Inc.) was added to 2.00 mL of $n$-$C_8F_{17}C_2H_5$ (F-Tech, Inc.) and the solution saturated with diazepam (Hoffman La Roche.). The resulting stable solution was filtered with a 0.20 µm (PTFE-polytetrafluoroethylene) filter and the diazepam concentration determined by UV/visible spectroscopy using an external standard curve. An absorbance band at $\lambda$=ca 252 nm was used for quantitation. The diazepam concentration was determined to be 123 mg/L in the perfluorochemical matrix.

EXAMPLE 2

Preparation of a Diazepam in Perfluoroalkyl Alkane (n-CmF2m+1 CnH2n+1) Solution

A diazepam-containing perfluorochemical solution was prepared as follows:

An aliquot of $n$-$C_mF_{2m+1}$—$C_nH_{2n+1}$ (2 mL; F-Tech, Inc.) was saturated with diazepam (Hoffman La Roche). The solution was filtered with a 0.20 µm (PTFE-polytetrafluoroethylene) filter and the diazepam concentration determined by UV/Visible spectroscopy using an exter-nal standard curve. An absorbance band at $\lambda$=ca 252 nm was used for quantitation.

| Perfluoroalkylalkane | mg/L of Diazepam in perfluorochemical matrix |
| --- | --- |
| $n$-$C_6F_{13}$ $C_2H_5$ | 150 |
| $n$-$C_6F_{13}$ $C_6H_{13}$ | 575 |
| $n$-$C_8F_{17}$ $C_2H_5$ | 85 |

EXAMPLE 3

Preparation of a Caffeine in Perfluoroalkyl Alkane (n-CmF2m+1 CnH2n+1) Solution

A caffeine containing perfluorochemical solution was prepared as follows:

An aliquot of $n$-$C_mF_{2m+1}$—$C_nH_{2n+1}$ (2 mL; F-Tech, Inc.) was saturated with caffeine (Sigma Chemical Co.). The solution was filtered with a 0.20 µm (PTFE-polytetrafluoroethylene) filter and the caffeine concentration determined by UV/Visible spectroscopy using an external standard curve. An absorbance band at $\lambda$=ca 275 nm was used for quantitation.

| Perfluoroalkylalkane | mg/L of Caffeine in perfluorochemical matrix |
| --- | --- |
| $n$-$C_6F_{13}C_2H_5$ | 14 |
| $n$-$C_8F_{17}C_2H_5$ | 6 |
| $n$-$C_8F_{17}C_4H_9$ | 8 |
| $n$-$C_8F_{17}C_6H_{13}$ | 11 |

EXAMPLE 4

Effect of Ethyl Alcohol Addition to a Caffeine in Perfluorooctyl Ethane (n-C8F17C2H5) Solution A caffeine containing perfluorochemical solution was prepared as follows:

An aliquot of $n$-$C_6F_{13}C_2H_5$ (2 mL; F-Tech, Inc.) containing increasing levels of ethyl alcohol (0, 0.5, 1, 2 and 3.3% -Spectrum Chemical Co.) was saturated with caffeine (Sigma Chemical Co.). The solution was filtered with a 0.20 µm (PTFE-polytetrafluoroethylene) filter and the caffeine concentration determined by UV/visible spectroscopy using an external standard curve. An absorbance band at $\lambda$=ca 275 nm was used for quantitation of the resulting stable solutions.

| % v/v of Ethyl Alcohol in $n$-$C_6F_{13}C_2H_5$ | mg/L of Caffeine in perfluorochemical matrix |
| --- | --- |
| 0 | 6 |
| 0.5 | 21 |
| 1 | 25 |
| 2 | 36 |
| 3.3 | 44 |

EXAMPLE 5

Solubility of Prednisone in Fluorocarbons

A prednisone containing perfluorochemical solution was prepared as follows:

An aliquot of $n$-$C_mF_{2m+1}C_nH_{2n+1}$ (2 mL; F-Tech, Inc.) having a concentration of 3% v/v of ethyl alcohol (Spectrum Chemical Co.), perfluorooctyl bromide (2 mL PFOB, Atochem, France) with 3% v/v of ethyl alcohol or 1,4-dibromooctafluorobutane (2 mL, Exfluor) with and without ethyl alcohol, was saturated with prednisone (Sigma Chemical Co.). The solution was filtered with a 0.20 $\mu$m (PTFE-polytetrafluoroethylene) filter and the prednisone concentration determined by an external standard curve using HPLC (Beckman System Gold). The column was a 25 cm amino column (Rainin), and the detection was carried out by a UV detector (Beckman System Gold) at the end of the column.

| Fluorochemical | mg/L of prednisone in fluorochemical matrix |
| --- | --- |
| 1,4-Dibromooctafluorobutane | <1 |
| n-$C_8F_{17}$Br with 3% Ethyl Alcohol | <1 |
| n-$C_6F_{13}C_2H_5$ with 3% Ethyl Alcohol | 27 |
| n-$C_6F_{13}C_6H_{13}$ with 3% Ethyl Alcohol | 80 |
| 1,4-Dibromooctafluorobutane with 10% Ethyl Alcohol | 1700 |
| 1,4-Dibromooctafluorobutane with 50% Ethyl Alcohol | 3800 |

EXAMPLE 6

Effect of log $P_{o/w}$ on the Solubility in Perfluorooctyl Ethane

A pharmaceutical fluorochemical solution was prepared as follows:

An aliquot of n-$C_8F_{17}C_2H_5$ (2 mL; F-Tech, Inc.) was saturated with "Drug" (Sigma Chemical Co.). The solution was filtered with a 0.20 $\mu$m (PTFE-Polytetrafluoroethylene) filter and the "Drug" concentration determined by UV/Visible spectroscopy using an external standard curve.

| | log $P_{o/w}$ | g/L in $C_8F_{17}C_2H_5$ |
| --- | --- | --- |
| Pyridine | 0.644 | 94.6 |
| Phenol | 1.469 | 2.9 |
| p-Cresol | 1.9 | 3.9 |
| o-Ethylphenol | 2.47 | 9.4 |
| Naphthalene | 3.387 | 8.1 |
| Butylbenzene | 4 | 115.7 |
| Antracene | 4.473 | 9E-02 |
| Hexylbenzene | 5.52 | 67.1 |
| 2,3 Benzanthracene | 5.807 | 3E-04 |
| m-Pentadecylphenol | 9.53 | 0.4 |

EXAMPLE 7

Effect of Fluorochemical Lipophilicity on Pharmaceutical Solubility

Pharmaceutical fluorochemical solutions were prepared as follows:

An aliquot of n-$C_mF_{2m+1}C_nH_{2n+1}$ (2 mL; F-Tech, Inc.) was saturated with naphthalene or pentadecylphenol (Sigma Chemical Co.). The solution was filtered with a 0.20 $\mu$m (PTFE-polytetrafluoroethylene) filter and the concentration determined by UV/visible spectroscopy using an external standard curve.

| | | Pharmaceutical Agent | |
| --- | --- | --- | --- |
| Fluorocarbon | $R_m$ | Naphthalene (g/L) | Pentadecylphenol |
| $C_6F_{13}C_2H_5$ | 41.99 | 12 | 0.7 |
| $C_6F_{13}C_6H_{13}$ | 60.42 | 30 | 4.1 |
| $C_6F_{13}C_8H_{17}$ | 69.64 | 40 | 5.6 |
| $C_8F_{17}C_2H_5$ | 52.62 | 8 | 0.4 |
| $C_8F_{17}C_4H_9$ | 61.83 | 14 | 0.6 |
| $C_8F_{17}C_6H_{13}$ | 71.04 | 23 | 1.7 |

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments which have been described in detail herein. Rather, reference should be made to the appended claims as indicative of the scope and content of the present invention.

What is claimed is:

1. A thermodynamically stable molecular solution providing enhanced bioavailability for lipophilic pharmaceutical agents, said molecular solution comprising:

a liquid carrier comprising one or more physiologically acceptable lipophilic fluorochemicals comprising four or more carbon atoms and at least one nonfluorinated co-solvent; and a pharmaceutically effective amount of at least one lipophilic pharmaceutical agent in said liquid carrier.

2. The thermodynamically stable molecular solution of claim 1, wherein said one or more physiologically acceptable lipophilic perfluorochemicals are selected from the group consisting of halogenated fluorochemicals, fluorocarbon-hydrocarbon diblock or triblock compounds, halogenated ethers, polyethers, fluorocarbon-hydrocarbon esters, fluorocarbon-hydrocarbon thioesters, fluorocarbon-hydrocarbon amines and fluorocarbon-hydrocarbon amides.

3. The thermodynamically stable molecular solution of claim 1 wherein said one or more physiologically acceptable lipophilic fluorochemicals are selected from the group consisting of: $C_nF_{2n+1}X$, $XC_nF_{2n}X$, where n=4–8, X=Br, Cl or I; $C_nF_{2n+1}$—$C_mH_{2m+1}$, $C_nF_{2n+1}CH$=$CHC_mH_{2m+1}$, where n=2–8 m=2–6; $C_pH_{2p+1}$—$C_nF_{2n}$—$C_mH_{2m+1}$, where p=2–6, m=2–6 and n=2–8; $XC_nF_{2n}OC_mF_{2m}X$, $XCF_2OC_nF_{2n}OCF_2X$, where n=1–4, m=1–4, X=Br, Cl or I; $C_nF_{2n}$—O—$C_mH_{2m+1}$, where n=2–8; m=2–6; $C_pH_{2p+1}$—O—$C_nF_{2n}$—O—$C_mH_{2m+1}$, where p=2–6, m=2–6 and n=2–8; 1-bromo-F-octane (n-$C_8F_{17}$Br); 1-bromo-F-heptane (n-$C_7F_{15}$Br); 1-bromo-F-hexane (n-$C_6F_{13}$Br); 1-bromo-F-pentane (n-$C_5F_{11}$Br); 1-bromo-F-butane (n-$C_4F_9$Br); perfluorooctyl chloride (n-C7$F_{15}$Cl); 1, 6-dichloro-F-hexane (n-Cl$C_6F_{12}$Cl); 1, 4-dichloro-F-butane (n-Cl$C_4F_8$Cl); 1, 4-dibromo-F-butane and 1,6-dibromo-F-hexane.

4. The thermodynamically stable molecular solution of claim 1 wherein said at least one lipophilic pharmaceutical agent is selected from the group consisting of respiratory agents, antibiotics, anti-inflammatories, antineoplastics, chemotherapeutic agents, anesthetics, ophthalmic agents, cardiovascular agents, imaging agents and combinations thereof.

5. The thermodynamically stable molecular solution of claim 1 wherein said at least one lipophilic pharmaceutical agent exhibits a log of the octanol/water partition coefficient (Log Po/w) greater than about 0.5.

6. The thermodynamically stable molecular solution of claim 1 wherein a therapeutically beneficial amount of a physiologically acceptable gas is incorporated in said liquid carrier.

7. The thermodynamically stable molecular solution of claim 1 wherein said at least one nonfluorinated co-solvent is selected from the group consisting of ethers, alcohols, alkyl sulfoxides, and combinations thereof.

8. The thermodynamically stable molecular solution of claim 7 wherein said one or more physiologically acceptable lipophilic perfluorochemicals is selected from the group consisting of halogenated fluorochemicals, fluorocarbon-hydrocarbon diblock or triblock compounds, halogenated ethers, polyethers, fluorocarbon-hydrocarbon esters, fluorocarbon-hydrocarbon thioesters, fluorocarbon-hydrocarbon amines and fluorocarbon-hydrocarbon amides.

9. The thermodynamically stable molecular solution of claim 7 wherein said at least one lipophilic pharmaceutical agent is selected from the group consisting of respiratory agents, antibiotics, anti-inflammatories, antineoplastics, chemotherapeutic agents, anesthetics, ophthalmic agents, cardiovascular agents, imaging agents and combinations thereof.

10. The thermodynamically stable molecular solution of claim 7 wherein the concentration of said at least one incorporated pharmaceutical agent is less than approximately 10% w/v and the concentration of said at least one co-solvent is less that approximately 50% v/v.

11. The thermodynamically stable molecular solution of claim 7 wherein said at least one co-solvent is ethanol, the physiologically acceptable lipophilic fluorochemical is 1,4-dibromo-F-butane and the concentration of said at least one incorporated lipophilic pharmaceutical agent is less than approximately 10% w/v.

12. A method for preparing a thermodynamically stable molecular solution exhibiting enhanced bioavailability, said method comprising the steps of:

providing a liquid carrier comprising one or more physiologically acceptable lipophilic fluorochemicals comprising four or more carbon atoms and at least one nonfluorinated co-solvent; and combining a pharmaceutically effective amount of at least one lipophilic pharmaceutical agent with said liquid carrier to form said thermodynamically stable molecular solution.

13. The method of claim 12 wherein said one or more physiologically acceptable lipophilic perfluorochemicals is selected from the group consisting of halogenated fluorochemicals, fluorocarbon-hydrocarbon diblock or triblock compounds, halogenated ethers, polyethers, fluorocarbon-hydrocarbon esters, fluorocarbon-hydrocarbon thioesters, fluorocarbon-hydrocarbon amines and fluorocarbon-hydrocarbon amides.

14. The method of claim 1 wherein said at least one lipophilic pharmaceutical agent is selected from the group consisting of respiratory agents, antibiotics, anti-inflammatories, antineoplastics, chemotherapeutic agents, anesthetics, ophthalmic agents, cardiovascular agents, imaging agents and combinations thereof.

15. The method of claim 12 wherein the concentration of said at least one lipophilic pharmaceutical agent is less than approximately 10% w/v.

16. The method of claim 12 wherein said lipophilic pharmaceutical agent exhibits a log of the octanol/water partition coefficient (Log Po/w) greater than about 0.5.

17. The method of claim 12 further comprising the step of introducing a therapeutically beneficial amount of a physiologically acceptable gas into said liquid carrier.

18. The method of claim 12 wherein said at least one nonfluorinated co-solvent is selected from the group consisting of ethers, alcohols, alkyl sulfoxides and combinations thereof.

19. The method of claim 18 wherein said at least one lipophilic pharmaceutical agent is selected from the group consisting of respiratory agents, antibiotics, anti-inflammatories, antineoplastics, chemotherapeutic agents, anesthetics, ophthalmic agents, cardiovascular agents, imaging agents and combinations thereof.

20. The method of claim 18 wherein the concentration of said at least one lipophilic pharmaceutical agent is less than approximately 10% w/v and the concentration of said at least one co-solvent is less than approximately 50% v/v.

21. A molecular solution prepared according to the method of claim 12.

22. A molecular solution prepared according to the method of claim 18.

23. A molecular solution prepared according to the method of claim 20.

24. A method for delivering at least one lipophilic pharmaceutical agent to a physiologic target site, said method comprising the steps of:

providing a thermodynamically stable molecular solution comprising at least one lipophilic pharmaceutical agent incorporated in a physiologically acceptable liquid carrier, said liquid carrier comprising one or more lipophilic fluorochemicals comprising four or more carbon atoms and at least one nonfluorinated co-solvent; and introducing a pharmaceutically effective amount of said thermodynamically stable molecular solution to a physiologic target site.

25. The method of claim 24 wherein said one or more lipophilic perfluorochemicals are selected from the group consisting of halogenated fluorochemicals, fluorocarbon-hydrocarbon diblock or triblock compounds, halogenated ethers, polyethers, fluorocarbon-hydrocarbon esters, fluorocarbon-hydrocarbon thioesters, fluorocarbon-hydrocarbon amines and fluorocarbon-hydrocarbon amides.

26. The method of claim 24 wherein said at least one lipophilic pharmaceutical agent is selected from the group consisting of respiratory agents, antibiotics, anti-inflammatories, antineoplastics, chemotherapeutic agents, anesthetics, ophthalmic agents, cardiovascular agents, imaging agents and combinations thereof.

27. The method of claim 24 wherein said at least one lipophilic pharmaceutical agent exhibits a log of the Octanol/water partition coefficient (Log Po/w) greater than about 0.5.

28. The method of claim 24 further comprising the step of introducing a therapeutically beneficial amount of a physiologically acceptable gas into said liquid carrier.

29. The method of claim 24 wherein said at least one nonfluorinated co-solvent is selected from the group consisting of ethers, alcohols, alkyl sulfoxides, and combinations thereof.

30. The method of claim 29 wherein said one or more physiologically acceptable lipophilic perfluorochemicals is selected from the group consisting of halogenated fluorochemicals, fluorocarbon-hydrocarbon diblock or triblock compounds, halogenated ethers, polyethers, fluorocarbon-hydrocarbon esters, fluorocarbon-hydrocarbon thioesters, fluorocarbon-hydrocarbon amines and fluorocarbon-hydrocarbon amides.

31. The method of claim 29 wherein said at least one lipophilic pharmaceutical agent is selected from the group consisting of respiratory agents, antibiotics, anti-inflammatories, antineoplastics, chemotherapeutic agents, anesthetics, ophthalmic agents, card vascular agents, imaging agents and combinations thereof.

32. The method of claim 24 wherein the introduction of said molecular solution to the physiological target site is accomplished topically, subcutaneously, intramuscularly, intraperitoneally, nasally, pulmonarily, vaginally, rectally, aurally, orally or ocularly.

33. The method of claim 24 wherein said physiological target site comprises the lung.

34. The method of claim 24 wherein said physiological target site comprises the eye.

35. The method of claim 24 wherein said physiological target site comprises the gastrointestinal tract.

* * * * *